United States Patent
De Souza et al.

(10) Patent No.: US 6,753,333 B2
(45) Date of Patent: *Jun. 22, 2004

(54) CHIRAL FLUOROQUINOLONE ARGININE SALT FORMS

(75) Inventors: Noel J. De Souza, Chikaltana (IN); Shivkumar Agarwal, Chikaltana (IN); Mahesh V. Patel, Chikaltana (IN); Satish B. Bhawsar, Chikaltana (IN); Rupinder K. Beri, Chikaltana (IN); Ravindra D. Yeole, Chikaltana (IN); Nitin Shetty, Chikaltana (IN)

(73) Assignee: Wockhardt Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 10/303,692

(22) Filed: Nov. 22, 2002

(65) Prior Publication Data

US 2003/0144517 A1 Jul. 31, 2003

Related U.S. Application Data

(62) Division of application No. 09/802,793, filed on Mar. 9, 2001, now Pat. No. 6,514,986.

(30) Foreign Application Priority Data

Nov. 21, 2000 (WO) ................................ PCT/IN00/00111

(51) Int. Cl.⁷ .................. A61K 31/4375; C07D 455/06; A61P 31/04
(52) U.S. Cl. ......................... 514/294; 546/94; 424/451; 424/456; 424/461; 424/474; 424/489
(58) Field of Search ............................. 546/94; 514/294

(56) References Cited

U.S. PATENT DOCUMENTS

| | | | |
|---|---|---|---|
| 3,924,042 A | 12/1975 | Gerster | 424/258 |
| 3,984,403 A | 10/1976 | Fujisawa et al. | 260/243 C |
| 3,985,882 A | 10/1976 | Gerster | 424/258 |
| 4,051,247 A | 9/1977 | Schuppan et al. | 424/258 |
| 4,399,134 A | 8/1983 | Ishikawa et al. | 424/246 |
| 4,404,207 A | 9/1983 | Stern | 424/258 |
| 4,416,884 A | 11/1983 | Ishikawa et al. | 424/250 |
| 4,443,447 A | 4/1984 | Gerster et al. | 424/248 |
| 4,472,406 A | 9/1984 | Gerster | 424/258 |
| 4,472,407 A | 9/1984 | Stern | 424/258 |
| 4,535,161 A | 8/1985 | Hayakawa | 546/94 |
| 4,552,879 A | 11/1985 | Ishikawa et al. | 514/253 |
| 4,594,347 A | 6/1986 | Ishikawa et al. | 514/252 |
| 4,599,418 A | 7/1986 | Irikura et al. | 544/361 |
| 4,642,355 A | 2/1987 | Nakamura et al. | 548/533 |
| 5,185,337 A | 2/1993 | Fujii et al. | 514/254 |
| 5,859,026 A | 1/1999 | Ito et al. | 514/312 |
| 5,889,009 A | 3/1999 | Miyake et al. | 514/254 |
| 6,034,100 A | 3/2000 | Adachi et al. | 514/312 |
| 6,121,285 A | 9/2000 | Takemura et al. | 514/312 |
| 6,184,388 B1 | 2/2001 | Takemura et al. | 548/566 |
| 6,329,391 B1 | 12/2001 | Ledoussal et al. | 514/312 |

FOREIGN PATENT DOCUMENTS

| | | |
|---|---|---|
| EP | 0908181 | 4/1999 |
| JP | 57081486 | 5/1982 |
| JP | 57176987 | 10/1982 |
| JP | 63192753 | 2/1987 |
| JP | 02131483 | 11/1988 |
| JP | 02188589 | 1/1989 |
| JP | 02188570 | 7/1990 |
| JP | 05339238 | 6/1992 |
| JP | 58090511 | 11/1992 |
| WO | 9420105 | 9/1994 |
| WO | 9744034 | 11/1997 |
| WO | WO 00/68229 | * 11/2000 |

OTHER PUBLICATIONS

Ball, P. "The Quinolones: History and Overview" *The Quinolones*, Second Ed., Chapter 1, p. 1–28, Academic Press, (1998).

Domagala, J.M. "Structure–activity and structure–side–effect relationships for the quinolone antibacterials" *J. Antimicrobial Chemotherapy*, vol. 33, p. 685–706, (1994).

Suto, M.J, et al. "Fluoroquinolones: Relationships between Structural Variations, Mammalian Cell Cytotoxicity, and Antimicrobial Activity" *J. Med. Chem.*, vol. 35, p. 4745–4750, (1992).

Abstract Yamakawa, T., et al. "In vitro and in vivo antibacterial activity of T–3912, a novel non–fluorinated topical quinolone" *J. Antimicrob Chemother*, vol. 49, No. 3, p. 455–465, (2002).

Hooper, D.C. "Mechanisms of fluoroquinolone resistance" *Drug Resistance Updates*, vol. 2, p. 38–55, (1999).

Ince, D., et al. "Mechanisms and Frequency of Resistance to Gatifloxacin in Comparison to AM–1121 . . . *Staphylococcus aureus*" *Antimicrob Agents and Chemother*, vol. 45, No. 10, p. 2755–2764 (2001).

Fournier, B., et al. "Mutations in Topoisomerase IV and DNA Gyrase of *Staphylococcus aureus*: Novel Pleiotropic Effects . . . Activity" *Antimicrob Agents and Chemother*, vol. 42, No. 1, p. 121–128 (1998).

Zhao, X., et al. "Killing of *Staphylococcus aureus* by C–8–Methoxy Fluoroquinolones" *Antimicrob Agents and Chemother*, vol. 42, No. 4, p. 956–958, (1998).

Breines, D.M, et al. "Quinolone Resistance Locus nfxD of *Escherichia coli* is a Mutant Allele of the parE . . . Topoisomerase IV" *Antimicrob Agents and Chemother*, vol. 41, No. 1, p. 175–179, (1997).

(List continued on next page.)

*Primary Examiner*—Evelyn Mei Huang
(74) *Attorney, Agent, or Firm*—Ladas & Parry (57) ABSTRACT

The invention relates to the new arginine salt forms of S-(−)-9-fluoro-6,7-dihydro-8-(4-hydroxypiperidin-1-yl)-5-methyl-1-oxo-1H,5H-benzo[i,j]quinolizine-2-carboxylic acid, a process for their preparation and pharmaceutical formulations which comprise those arginine salt forms as the active ingredient for its use in treating antimicrobial infections.

4 Claims, 6 Drawing Sheets

OTHER PUBLICATIONS

Fournier, B., et al. "Expression of the Multidrug Resistance Transporter NorA from *Staphylococcus aureus* is Modified . . . System" *J. Bacteriology*, vol. 182, No. 3, p. 664–671 (2000).

Mandell, L.A, et al. "Antimicrobial Safety and Tolerability: Differences and Dilemmas" *CID*, vol. 32, Suppl 1, p. S72–S79, (2001).

Gootz, T.D., et al. "Chemistry and Mechanism of Action of the Quinolone Antibacterials" *The Quinolones*, Second Edition, Chapter 2, p. 29–80, Academic Press (1998).

Takenouchi, T., et al. "Hydrophilicity of Quinolones Is Not an Exclusive Factor for Decreased Activity in . . . *Staphylococcus aureus*" *Antimicrob Agents and Chemother*, vol. 40, p. 8, p. 1835–1842, (1996).

Zhao, X, et al. "DNA topoisomerase targets of the fluoroquinolones: A strategy for avoiding bacterial resistance" *Proc. Natl. Acad. Sci. USA*, vol. 94, p. 13991–13996, (1997).

Takei, M., et al. "Target Preference of 15 Quinolones against *Staphylococcus aureus*, based on Antibacterial . . . Inhibition" *Antimicrob Agents and Chemother*, vol. 45, No. 12, p. 3544–3547, (2001).

Ince, D., et al. "Mechanisms and Frequency of Resistance to Premafloxacin in *Staphylococcus aureus*: Novel . . . Interactions" *Antimicrob Agents and Chemother*, vol. 44, No. 12, p. 3344–3350, (2000).

Oizumi, N., et al. "Relationship between mutations in the DNA gyrase and topoisomerase IV genes . . . *Staphylococcus aureus*" *J. Infect. Chemother*, vol. 7, p. 191–194, (2001).

Asahina, Y., et al. "Recent advances in structure activity relationships in new quinolones" *Progress in Drug Research*, vol. 38, p. 57–106, (1992).

Sloan, G.J., et al in Physics and Chemistry of the Organic Solid State, Edited by D Fox, MM Labes & Weissberger. Interscience Publishers, (1963)pp179–182.

Berge, S.M. et al. J. Pharm. Sci. (1977) 66 (1), 1–19.

English Abstract of Japanese Patent JP 02131483 dated Nov. 1988.

English Abstract of Japanese Patent JP 02188589 dated Jan. 1989.

Abstract: Koike, M. et al. "Metabolic Fate of (.+–.)–9–fluoro–6,7–dihydro–8–(4–hydroxy–1–piperidyl) . . . Rabbits and Dogs" *Iyakuhin Kenkyu* vol. 21, No. 5 (1990) pp. 998–1021.

Abstract: Koike, M. et al. "Metabolic Fate of (.+–.)–9–fluoro–6,7–dihydro–8–(4–hydroxy–1–piperidyl) . . . Rabbits and Dogs" *Iyakuhin Kenkyu* vol. 21, No. 5 (1990) pp. 1022–1033.

Abstract: Fujita, S. et al. "General Pharmacology of (.+–.)–9–fluoro–6,7–dihydro–8–(4–hydroxy–1–piperidyl) . . . antibacterial agent" *Iyakuhin Kenkyu* vol. 21, No. 6 (1990) pp. 1156–1176.

Abstract: Koike, M. et al. "The Distribution of OPC–7251 in the Skin" *Yakubutsu Dotai* vol. 5, No. 2 (1990) pp 199–208.

Abstract: Yasuo, A. et al. "Pharmacokinetics and Safety Evaluation of OPC–7251 Cream After Topical . . . Volunteers" *Yakuri to Chiryo* vol. 18, No. 4 (1990) pp 1717–1730.

Abstract: Hayakawa, R. et al. "Safety Evaluation of Topical OPC–7251 (Synthetic Antibacterial Agent)" *Hifu* vol. 32, No. 2 (1990) pp 217–230.

Abstract: Asada, Y. et al. "Pharmacokinetics and Toxicity of OPC–7251 Cream After Topical Applications . . . Volunteers" *Yakuri to Chiryo* vol. 18, No. 4 (1990) pp 1717–1730.

Abstract: Awogi, T. et al. "Genotoxicity Studies of (.+–.)–9–fluoro–6,7–dihydro–8–(4–hydroxy–1–piperidyl) . . . Antibacterial Agent" *Iyakuhin Kenkyu* vol. 21, No. 4 (1990) pp. 626–635.

Abstract: Matsuzawa, A. et al. "Reproductive and Developmental Toxicity Studies of (.+–.)–9–fluoro–6,7–dihydro–. . . Agent" *Iyakuhin Kenkyu* vol. 21, No. 4 (1990) pp. 636–646.

Abstract: Nagao, T. et al. "Reproductive and Development Toxicity Studies Of (.+–.)–9–fluoro–6,7–dihydro–8–. . . Administration" *Iyakuhin Kenkyu* vol. 21, No. 4 (1990) pp. 647–662.

Abstract: Matsuzawa, A. et al. "Reproductive and Developmental Toxicity Studies Of (.+–.)–9–fluoro–. . . Administration" *Iyakuhin Kenkyu* vol. 21, No. 4 (1990) pp. 663–670.

Abstract: Hashimoto, K. et al. "Acute Toxicity Study of the Synthetic Antibacterial Topical Agent (.+–.)–9–fluoro–6,7–. . . Acid (OPC–7251)" *Iyakuhin Kenkyu* vol. 21, No. 4 (1990) pp. 670–677.

Abstract: Furukawa, M. et al. "Primary Skin Irritation, Four–Week Cumulative Skin Irritation, . . . 1% OPC–7251 Cream" *Iyakuhin Kenkyu* vol. 21, No. 5 (1990) pp. 989–997.

Abstract: Kojima, K. et al. "Thirteen–Week Subcutaneous Toxicity and Four–Week Recover Tests . . . (OPC–7251) in Rats" *Iyakuhin Kenkyu* vol. 21, No. 5 (1990) pp. 1034–1052.

Abstract: Nakagiri, N. et al. "Contact Sensitivity, Photocontact Sensitivity And Antigenicity Tests . . . Antibacterial Agent" *Iyakuhin Kenkyu* vol. 21, No. 6 (1990) pp. 1144–1155.

Abstract: Aoki, M. et al. "Thirteen–Week Percutaneous Toxicity And Four–Week Recovery Tests . . . (OPC–7251) in Dogs" *Iyakuhin Kenkyu* vol. 21, No. 6 (1990) pp. 1177–1202.

Abstract:Matsuzawa, A. et al. "Reproductive And Development Toxicity Studies of . . . Administration" *Iyakuhin Kenkyu* vol. 22, No. 1 (1990) pp. 61–76.

Abstract: Kurokawa, I. et al. "Clinical And Bacteriologic Evaluation of OPC–7251 in Patients With Acne: . . . Cream Base" *J. Am. Acad. Dermatol.* vol. 25, No. 4 (1991) pp 674–681.

Abstract: Bojar, R. A. et al. "Analysis of Resistance In The Cutaneous Microflora During Treatment Of Acne–. . . Erythromycin" *J. of Investigative Dermatology* vol. 103, No. 3 (1994) pp 405.

Hashimoto, K. et al. "A Practical Synthesis of (S)–(–)–Nadifloxacin: Novel Acid–Catalyzed Racemization . . . " *Chem. Pharm. Bull.* vol. 44 No. 4 (1996) pp 642–645.

Irish, D. et al. "Control of an Outbreak of an Epidemic Methicillin–Resistant *Staphylococcus aureus* also Resistant to Mupirocin" *Journal of Hospital Infection* vol. 39 (1998) pp 19–26 (XP–000884368).

Kido, M. et al. "Crystal Structures of Nadifloxacin Anhydride and Its Hemihydrate" *Chem. Pharm. Bull.* vol. 42 No. 4 (1994) pp 872–876.

Kido, M. et al. "The Absolute Configuration of (R)–(+)–Nadifloxacin" *Chem. Pharm. Bull.* vol. 44 No. 2 (1996) pp 421–423.

English Abstract of Japanese Patent J05339238 Dated Jun. 1992.

English Abstract of Japanese Patent J58090511 Dated Nov. 1992.

English Abstract of Japanese Patent J63192753 Dated Feb. 1987.

English Abstract of Japanese Patent JP57081486 Dated May 1982.

English Abstract of Japanese Patent 57–176987 Dated Oct. 1982.

English Abstract of Japanese Patent 02188570 Dated Jul. 1990.

Miller, M.A. et al. "Development of Mupirocin Resistance Among Methicillin–Resistant *Staphylococcus aureus* . . . " *Infection Control and Hospital Epidemiology* vol. 17 No. 12 (1995) pp 811–813 (XP–000884374).

Nishijima, S. et al. "Sensitivity of *Staphylococcus aureus*, Isolated from Skin Infections in 1994, to 19 Antimicrobial Agents" *The Journal of Int'l Medical Research* vol. 23 (1995) pp 328–334 (XP–000884323).

Nishijima, S. et al. "Activity of Eight Fluoroquinolones Against Both Methicillin–Susceptible and –Resistant *Staphylococcus aureus* . . . " *Journal of Dermatology* vol. 22 (1995) pp 153–155 (XP–000884341).

Nishijima, S. et al. "Activity of Nadifloxacin Against Methicillin–Resistant *Staphylococcus aureus* Isolated from . . . " *The Journal of Int'l Medical Research* vol. 24 (1996) pp 12–16 (XP–000884325).

Nishijima, S. et al. "Sensitivity of *Staphylococcus aureus* and *Streptococcus pyogenes* Isolated from Skin Infections in 1992 to . . . " *Journal of Dermatology* vol. 21 (1994) pp 233–238 (XP–000884342).

UDO, E.E. et al. "Emergence of High–Level Mupirocin Resistance In Methicillin–Resistant *Staphylococcus aureus* in Western Australia" *J. of Hospital Infection* vol. 26 (1994) pp 157–165 (XP–000884369).

Abstract of Kurokawa, I. et al. "Antimicrobial Susceptibility of Propionibacterium Acnes Isolated From Vulgaris" *European Journal of Dermatology* vol. 9, No. 1 (1999) pp 25–28.

Abstract of Komagata, Y. et al. "Fundamental Studies On Antibacterial Activity Of Clindamycin Against Propionibacterium Acnes" *Japanese Journal of Antibiotics* vol. 51, No. 2 (1998) pp 130–136.

Abstract of Gollnick, H. et al. "Topical Drug Treatment In Acne" *Dermatology* vol. 196, No. 1 (1998) pp 119–125.

Abstract of Nishijima, S. et al. "Sensitivity of Antibacterials of *Staphylococcus aureus* Isolated From Impetigo Patients" *Journal of Int'l Medical Research* vol. 25, No. 4 (1997) pp 210–213.

Abstract of Nishijima, S. et al. "Sensitivity of Propionibacterium Acnes Isolated From Acne Patients: Comparative Study Of . . . " *Journal of Int'l Medical Research* vol. 24, No. 6 (1996) pp 473–477.

Abstract of Akamatsu, H. et al. "Effect of Nadifloxacin On Neutrophil Functions" *Journal of Int'l Medical Research* vol. 23, No. 1 (1995) pp 19–26.

Abstract of Takahashi, N. et al. "Reduction of In Vitro Clastogenicity Induced By The Mixture of Optical Isomers of Nadifloxacin During Storage" *Arzneimittel–Forschung* vol. 45, No. 2 (1995) pp 195–.

Abstract of Takahashi, N. et al. "In Vitro Clastogenicity of Optical Isomers of Nadifloxacin" *Arzneimittel–Forschung* vol. 44, No. 11 (1994) pp 1265–1268.

Abstract of Patel, M.V. "S–(–)–Nadifloxacin: Oral Bioavailability And Bioefficacy in Mouse Model of *Staphylococcal Septicemia*" 39th ICAAC at San Diego Poster No. F0558 (Sep. 26–29, 1999).

Chemical Abstract: Vogt, K. et al. "Antimicrobial Evaluation Of Nadifloxacin (OPC–7251), A New Topical Quinolone, In . . . " *Drugs* vol. 49, Suppl. 2 (1995) pp 266–268.

Chemical Abstract: Nishijima, S. et al. "In Vitro Activity of Nadifloxac Both Methicillin–Susceptible and –Resistant Clinical . . . " *Drugs* vol. 49, Suppl.2 (1995) pp 230–232.

Chemical Abstract: Bojar, R.A. et al. "Direct Analysis Of Resistance In T Cutaneous Microflora During Treatment Of Acne Vulgaris . . . " *Drugs* vol. 49, Suppl.2 (1995) pp 164–167.

Chemical Abstract: "An Efficient Synthesis of A Key Intermediate Toward (S)–(–)–Nadifloxacin" *Tetrahedron: Asymmetry* vol. 6, No. 1 (1995) pp 245–254.

Chemical Abstract: Vogt, K. et al. "Comparative Activity of the Topical Quinolone OPC–7251 Against . . . " *Eur. J. Clin. Microbiol. Infect. Dis.* vol. 11, No. 10 (1992) pp 943–945.

Chemical Abstract: Morita, S. et al. "Synthesis and Antibacterial Activit of the Metabolites . . . " *Chem. Pharm. Bull.* vol. 38, No. 7 (1990) pp 2027–2029.

Chemical Abstract: Muto, N. et al. "Development of a Sensitive Enzyme Immunoassay for OPC–7251, A Novel Antimicrobial . . . "*J. Immunoassay* vol. 11, No. 1 (1990) pp 1–16.

Chemical Abstract: Koike, M. et al. "High–Performance Liquid Chromatographic Procedure For The Determination . . . " *J. Chromatogr.* vol. 526, No. 1 (1990) pp 235–239.

Chemical Abstract: Ishikawa, H. et al. "Studies on Antibacterial Agents Synthesis of Substituted . . . " *Chem. Pharm. Bull.* vol. 37, No. 8 (1989) pp. 2103–2108.

Chemical Abstract: "Bacteriological Evaluation of OPC–7251, a new Pyrido Carboxylic Acid Antimicrobial Agent . . . " *Chemotherapy* vol. 37, No. 9 (1989) pp1160–1178.

Abstract of Iwahara, K. et al. "Tufted Hair Folliculitis: Response to Topical Therapy with Nadifloxacin" *European J. of Dermatology* vol. 9, No. 4 (1999) pp 276–277.

Abstract of Komagata, Y. et al. "Fundamental Studies On Antibacterial Activity of Clindamycin Against Propionibacterium Acnes" *Japanese J. of Antibiotics* vol. 51, No. 2, (1998) pp 130–136.

Abstract of Radl, S. "From Chloroquine To Antineoplastic Drugs? The Story of Antibacterial Quinolones" *Archiv der Pharmazie* vol. 329, No. 3 (1996) pp 115–119.

Abstract of Andriole, V.T. "The Future of the Quinolones" *Drugs* vol. 46, Suppl. 3 (1993) pp 1–7.

Abstract of Kurokawa, I. et al. "Clinical and Bacteriologyic Evaluation of OPC–7251 in Patients With Acne: A Double–Blinde Group . . . " *J. Amer. Acad. Of Dermatology*, vol. 25, No. 4 (1991) pp 674–681.

Abstract: Haustein, U.F. et al. "Topical Quinolone Nadifloxacin (OPC–7251 ) In Bacterial Skin Disease . . . Testing" *J. of Dermatological Treatment* vol. 8, No. 2 (1997) pp87–92.

Abstract: Smith, C.M. et al. "Influence of Different Formulations on the Efficacy of Topical Nadifloxacin (OPC–7251)" *J. of Investigative Dermatology* vol. 108, No. 3 (1997) pp 123.

Abstract: Hayakawa, R. et al. "Skin Safety Evaluation of Nadifloxacin (OPC–7251)" *Hifu* vol. 40, No. 2 (1998) pp 165–171.

Abstract: Fujio, N. et al. "Absorption, Distribution and Excretion of 14C–Labeled OPC–7251 Lotion In Rats" *Yakuri to Chiryo* vol. 26, No. 7 (1998) pp 1119–1132.

Takahashi, et al. "Optical isomers of nadifloxacin" Arzheim–Forsch/Drug Res., 45 (1), Nr. 2 (1995), pp 199–197.

Morita, S., et al "An Efficient Synthesis of a Key Intermediate towards ( (−) Tetrahedroni" Asymmetry, vol. 6 No. 1, pp 245–254 (1995).

Ishikawa et al. Chem, Pharm. Bull, 37 (8) 2103–2108 (1989).

Oizumi, N., et al. "Relationship between mutations in the DNA gyrase and topoisomerase IV genes and nadifloxacin . . . Staphylococcus aureus" *J. Infect Chemotherapy*, vol. 7, p. 191–194, (2001).

Haustein, U–F., et al. "Topical quinolone nadifloxacin (OPC–7251) in bacterial skin disease: clinical evaluation . . . testing" *J. of Dermatological Treatment*, vol. 8, p. 87–92, (1997).

English translation of Yamada, H., et al. "Evaluation of the in vitro drug efficacy of Nodifloxacin Cream" Iyakuhin Kenkyu, vol. 31, No. 8, p. 519–524, (2000).

English translation of Yamada, H., et al. "Bioequivalency of 1% Nadifloxacin lotion and 1% of Nadifloxacin cream" Iyakuhin Kenkyu, vol. 31, No. 8, p. 525–528, (2000).

* cited by examiner

CHIRAL FLUOROQUINOLONE ARGININE SALT FORMS

This application is a divisional of U.S. patent application Ser. No. 09/802,793 filed on Mar. 9, 2001 now U.S. Pat. No. 6,514,986.

FIELD OF THE INVENTION

The present invention relates to valuable new forms of a chiral fluoroquinolone, viz. arginine salt forms thereof, a novel process for manufacturing the novel arginine salt forms of the chiral fluoroquinolone, the use of the novel forms of the arginine salt of the chiral fluoroquinolone in the manufacture of pharmaceutical formulations and the use of the novel forms of the arginine salt of the chiral fluoroquinolone in medicine. More particularly, it relates to arginine salt forms of S-(−)-9-fluoro-6,7-dihydro-8-(4-hydroxypiperidin-1-yl)-5-methyl-1-oxo-1H,5H-benzo[ij] quinolizine-2-carboxylic acid, a process for preparing the same and their use in pharmaceutical formulations and medicine.

BACKGROUND OF THE INVENTION

The chiral fluoroquinolone known under the name S-(−)-9-fluoro-6,7-dihydro-8-(4-hydroxypiperidin-1-yl)-5-methyl-1-oxo-1H,5H-benzo[i,j] quinolizine-2-carboxylic acid is described in JP Patent 63,192,753A, JP Patent 05,339,238A, and in our pending U.S. patent applications Ser. Nos. 09/566,875 and 09/640,947, WO 00/68229 and PCT Application No. PCT/IN00/00111.

S-(−)-9-fluoro-6,7-dihydro-8-(4-hydroxypiperidin-1-yl)-5-methyl-1-oxo-1H,5H-benzo[i,j] quinolizine-2-carboxylic acid is an optically active isomer of the racemic compound which is claimed in U.S. Pat. No. 4,399,134. Although S-(−)-9-fluoro-6,7-dihydro-8-(4-hydroxypiperidin-1-yl)-5-methyl-1-oxo-1H,5H-benzo[i,j]quinolizine-2-carboxylic acid is not presently an ingredient of any commercial product, it is potentially useful as a commercial antimicrobial agent.

S-(−)-9-fluoro-6,7-dihydro-8-(4-hydroxypiperidin-1-yl)-5-methyl-1-oxo-1H,5H-benzo[i,j] quinolizine-2-carboxylic acid has an aqueous solubility of 0.8–2.0 mg/ml over the pH range 8.0–9.5 at 28° C., thus creating problems in having to formulate the drug as a tablet or capsule, or in making formulations for gavage and parenteral injection. The need for a salt is clearly indicated, as the lack of an appropriate salt form can hinder the development of dosage forms acceptable for systemic use in mammals.

S-(−)-9-fluoro-6,7-dihydro-8-(4-hydroxypiperidin-1-yl)-5-methyl-1-oxo-1H,5H-benzo [i,j]quinolizine-2-carboxylic acid has a pKa value of 6.80 suggesting a weak acid character and thus an ability to form a salt with an appropriate base. Generally, conversion of a pharmacologically active compound into a salt form induces a change in the compound's physicochemical properties such as solubility, absorption velocity, etc. Pharmaceutically more desirable salt forms may be selected by studying whether or not a crystalline or amorphous form, or polymorph or pseudopolymorph can be produced, and determining the properties including its physicochemical or biological properties. A pseudopolymorph is a polymorph that differs from a true polymorph by the incorporation of solvent (Solid-state Chemistry of Drugs, $2^{nd}$ Ed. S. R. Byrn et al (Eds). SSCI, Inc. 1999, p-514).

Pharmaceutically acceptable salts of racemic 9-fluoro-6,7-dihydro-8-(4-hydroxypiperidin-1-yl)-5-methyl-1-oxo-1H, 5H-benzo[i,j] quinolizine-2-carboxylic acid such as salts with inorganic bases and organic bases are mentioned in the text of Otsuka's U.S. Pat. No. 4,399,134. Besides salts with inorganic bases and organic bases, amino acid salts of S-(−)-9-fluoro-6,7-dihydro-8-(4-hydroxypiperidin-1-yl)-5-methyl-1-oxo-1H,5H-benzo[i,j] quinolizine-2-carboxylic acid are identified in our pending U.S. patent applications Ser. Nos. 09/566,875 and 09/640,947, WO 00/68229 and PCT Application No. PCT/IN00/00111. The subject matter of these applications is incorporated herein by reference.

S-(−)-9-fluoro-6,7-dihydro-8-(4-hydroxypiperidin-1-yl)-5-methyl-1-oxo-1H,5H-benzo[i,j]quinolizine-2-carboxylic acid, L-arginine salt 0.25 hydrate and S-(−)-9-fluoro-6,7-dihydro-8-(4-hydroxypiperin-1-yl)-5-methyl-1-oxo-1H,5H-benzo [i,j]quinolizine-2-carboxylic acid, L-arginine salt, 0.75 hydrate described in Examples 7 and 8 of U.S. patent applications Ser. Nos. 09/566,875 and 09/640,947, WO 00/68229 and PCT Application No. PCT/IN00/00111 respectively are highly hygroscopic and turn into syrups on exposure at a relative humidity of 41%. This presents major problems in bulk or manufacturing scale. Many hydrates and salts associated with water are susceptible to changes in humidity, are hygroscopic under adverse storage conditions and during pharmaceutical processing of them to medicament forms.

Amino acid salts, inorganic base and alkali salts and organic base salts of S-(−)-9-fluoro-6,7-dihydro-8-(4-hydroxypiperidin-1-yl)-5-methyl-1-oxo-1H,5H-benzo [i,j] quinolizine-2-carboxylic acid were prepared and studied by the inventors and it was found that:

(a) the arginine salt may exist in either a substantially crystalline form or a substantially amorphous form, each form having distinctive physicochemical, solubility and stability properties;

(b) the arginine salt is less prone than the sodium salt to absorb moisture at specified humidity levels;

(c) the arginine salt, whether crystalline or amorphous, possesses a lower propensity to cause phlebitis than the sodium and potassium salts as determined in rats by intravenous administration; and (d) the arginine salt is less toxic in rodents than the alkali salt forms.

In summary, the substantially crystalline form and substantially amorphous form of the arginine salt of S-(−)-9-fluoro-6,7-dihydro-8-(4-hydroxypiperidin-1-yl)-5-methyl-1-oxo-1H,5H-benzo[i,j]quinolizine-2-carboxylic acid have been found by the inventors to have very desirable properties in possessing under specified conditions, less hygroscopicity, favourable aqueous solubility, a low propensity to cause phlebitis, and favourable acute toxicity values. These forms are expected to be very useful as pharmaceutical agents as compared with the sodium salt, other inorganic base/alkali salts, organic base salts and other aminoacid salts. These advantages will be apparent from the experimental data shown hereafter.

SUMMARY OF THE INVENTION

The main objective of the invention accordingly relates to new arginine salts of S-(−)-9-fluoro-6,7-dihydro-8-(4-hydroxypiperidin-1-yl)-5-methyl-1-oxo-1H,5H-benzo[i,j] quinolizine-2-carboxylic acid of the formula I Formula I in which x denotes 0, 0.25, 0.5, 0.75, or 1.0, compositions comprising these salts, methods for preparing these salts and their use in medicine.

Another object of the present invention is to provide novel forms of the arginine salt of S-(−)-9-fluoro-6,7-dihydro-8-(4-hydroxypiperidin-1-yl)-5-methyl-1-oxo-1H,5H-benzo[i,j] quinolizine-2-carboxylic acid which can be used in full scale manufacturing of pharmaceutical formulations.

Still another object of the present invention is to provide a process for bulk scale production of S-(−)-9-fluoro-6,7-dihydro-8-(4-hydroxypiperidin-1-yl)-5-methyl-1-oxo-1H, 5H-benzo [i,j] quinolizine-2-carboxylic acid arginine salts of this invention.

A further object of the present invention to provide antibacterial compositions comprising the S-(−)-9-fluoro-6,7-dihydro-8-(4-hydroxypiperidin-1-yl)-5-methyl-1-oxo-1H, 5H-benzo[i,j]quinolizine-2-carboxylic acid arginine salt forms as an active component.

BRIEF DESCRIPTION OF THE DRAWINGS

The invention will now be described in further detail with reference to the accompanying drawings.

DISCLOSURE OF THE INVENTION

The invention accordingly relates to new arginine salts of S-(−)-9-fluoro-6,7-dihydro-8-(4-hydroxypiperidin-1-yl)-5-methyl-1-oxo-1H,5H-benzo[i,j] quinolizine-carboxylic acid of the formula I Formula I in which x denotes 0, 0.25, 0.5, 0.75, or 1.0.

These salts have favourable aqueous solubility, are stable in humid conditions, have favorable bioavailability, have a lower propensity to cause phlebitis and lower toxicity when administered in mammals.

This invention also relates to a process for the preparation of the salts, to their use in pharmaceutical compositions and in medicine.

A preferred arginine isomer is the S-isomer, that is L-arginine.

A preferred arginine salt is substantially an anhydrate wherein x=0. This anhydrate can exist in two polymorphic forms, one described as a substantially amorphous form (hereinafter amorphous form) and the other described as a substantially crystalline form (hereinafter crystalline form). The arginine salts of this invention are described as substantially crystalline or substantially amorphous because the degree of crystallinity of the crystalline form is not 100% and there is a degree of crystallinity in the amorphous form (see FIG. 2). Each of the two forms are shown to have distinct physicochemical properties, are more stable to decomposition from uptake of moisture at specified conditions, are distinguished by increased stability, in particular during storage at specified humidities and can be dried without caking or decomposing at elevated temperatures under reduced pressure. Both forms are particularly suitable for the preparation of stable pharmaceutical preparations, and have favourable biological properties.

Both forms, while less hygroscopic than the compounds of Examples 7 and 8 of U.S. patent applications Ser. Nos. 09/566,875 and 09/640,947, WO 00/68229 and PCT Application No. PCT/IN/00/00111, are to a certain degree hygroscopic. In stability studies at varying relative humidity conditions, both forms were found to remain stable at relative humidity values of 22% at 25° C. In stability studies at elevated temperatures, both forms remained stable with no decomposition up to 70° C., however, there was reduction in levels of water content and solvent content. On drying the forms at elevated temperatures over different periods of time and under different humidity conditions, the amounts of water found associated with the salt are altered. However, there is no change in the XRD-patterns of the forms. Without being bound to any theory, from this the inventors infer that the forms are substantially anhydrates and the values of the superficial amounts of associated water are amount due to the hygroscopic nature of the salt and not to the inventors knowledge to any incorporation of water in the lattice structure of the crystal water. The amorphous form tends to be slightly more hygroscopic than the crystalline form.

An anhydrate crystal form is a form that contains no solvent of crystallization (Solid-State Chemistry of Drugs, second edition, Stephen R. Byrn, Ralph R. Pfeiffer and Joseph Stowell, SSCI, Inc. West Lafayette, Ind.). Hydrates are said to exist when the drug substance incorporates water in the crystal lattice in either stochiometric or non-stochiometric amounts" (Stephen Byrn, et.al., Pharmaceutical Solids: A strategic Approach to Regulatory Considerations, Pharma. Res. Vol. 12 (7), 1995, 945–954).

The inventors have found that S-(−)-9-fluoro-6,7-dihydro-8-(4-hydroxypiperidin-1-yl)-5-methyl-1-oxo-1H, 5H-benzo [i,j] quinolizine-2-carboxylic acid arginine salt forms of this invention, have acceptable aqueous solubility of 1 mg/ml extending to 40 mg/ml, depending on the form, over the pH range 8.0–9.5 at ambient temperatures. The solubility of the crystalline form is 4.0 to 6.0 mg/ml at pH 9.5. The solubility of the amorphous form is 38.0 to 40.0 mg/ml at pH 9.5. The arginine salt forms are stable on heating at temperatures up to 65–70° C. at relative humidity ranges up to 22%. They have an acceptable dissolution rate.

The combination of physical properties of the novel S-(−)-9-fluoro-6,7-dihydro-8-(4-hydroxypiperidin-1-yl)-5-methyl-1-oxo-1H,5H-benzo[i,j]quinolizine-2-carboxylic acid arginine salt forms of the present invention with respect to the degree of crystallinity, particle diameter, density, hygroscopicity, water content and content of other solvents are favourable and permit the manufacturing of S-(−)-9-fluoro-6,7-dihydro-8-(4-hydroxypiperidin-1-yl)-5-methyl-1-oxo-1H,5H-benzo[i,j]quinolizine-2-carboxylic acid arginine salt in a composition which possesses the desired properties.

The properties of the crystalline and amorphous forms including the melting points are of values that endow the forms with desirable compression and flow properties for the processing of dosage forms useful for medicinal purposes.

The crystalline and amorphous forms of S-(−)-9-fluoro-6,7-dihydro-8-(4-hydroxypiperidin-1-yl)-5-methyl-1-oxo-1H,5H-benzo [i,j]quinolizine-2-carboxylic acid arginine salt also have desirable physicochemical properties as hereinbefore mentioned, and are characterised by parameters such as XRD, DSC, particle size and powder density.

Figure 1:
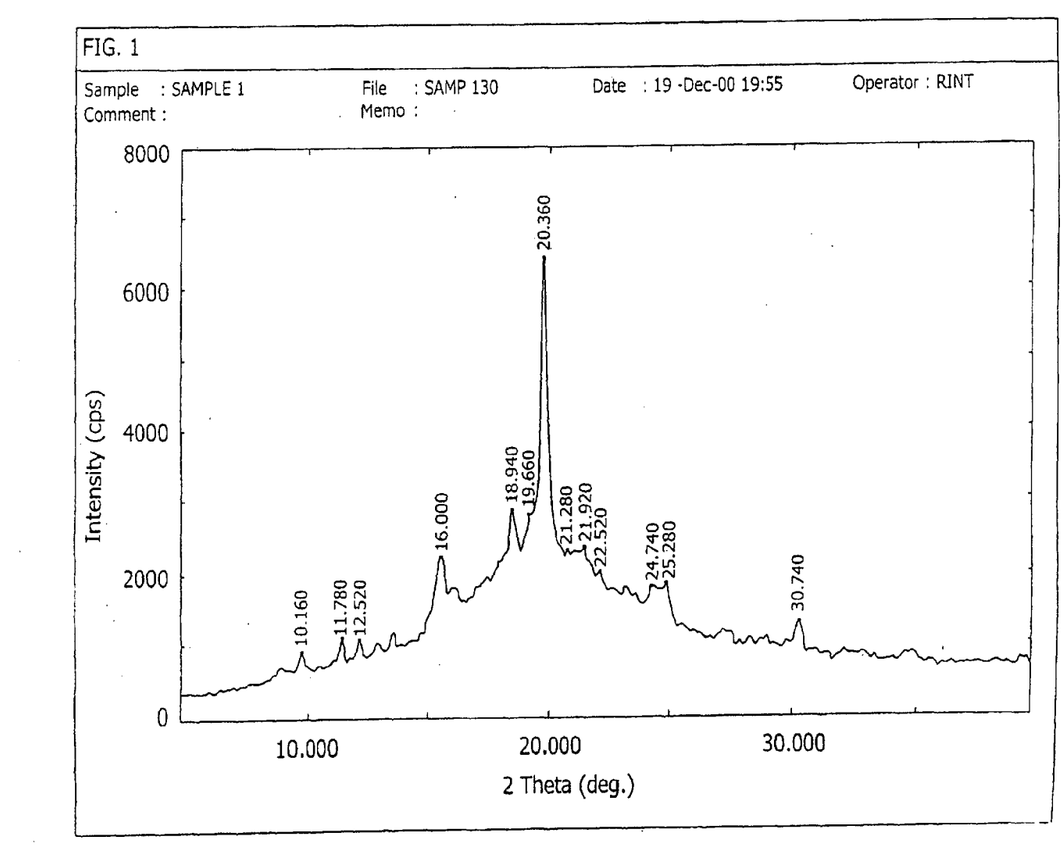
FIG. 1 represents the X-Ray Powder Diffraction (XRPD) spectrum of the substantially crystalline form of S-(−)-9-fluoro-6,7-dihydro-8-(4-hydroxypiperidin-1-yl)-5-methyl-1-oxo-1H,5H-benzo[i,j]quinolizine-2-carboxylic acid arginine salt of the invention.

The substantially crystalline form is described below:

(a) The degree of crystallinity as determined by X-ray powder diffraction is shown in FIG. 1, X-ray powder diffraction (2θ): 10.16, 11.78, 12.52, 16.00, 18.94, 19.66, 20.36, 21.28, 21.92, 22.52, 24.74, 25.28, 30.74.

Figure 3:
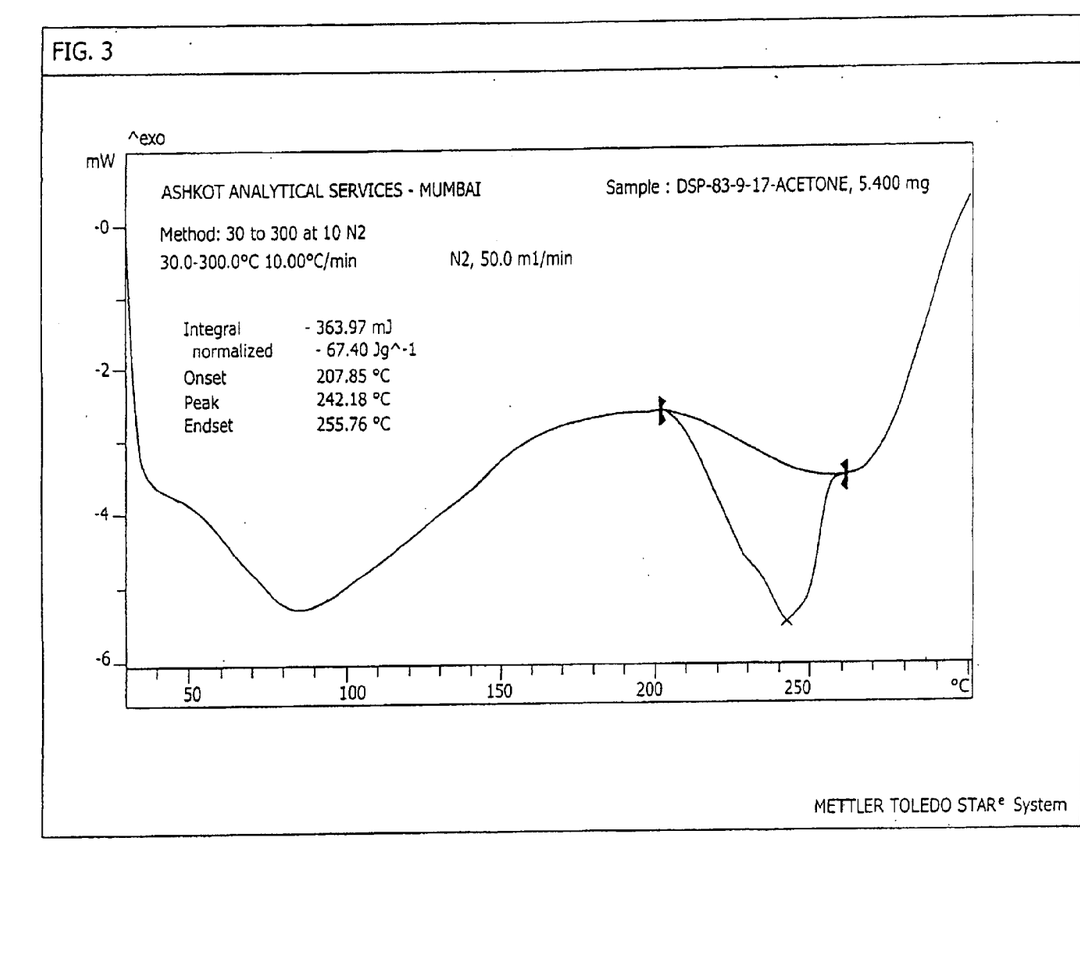
FIG. 3 represents the Differential Scanning Calorimeter (DSC) thermogram of the substantially crystalline form of S-(−)-9-fluoro-6,7-dihydro-8-(4-hydroxypiperidin-1-yl)-5-methyl-1-oxo-1H,5H-benzo[i,j]quinolizine-2-carboxylic acid arginine salt of the invention.

(b) A thermogram as determined by Differential scanning calorimetry is shown in FIG. 3 (DSC exotherm at 242.18° C. (onset at 207.85° C.)).

Figure 5:
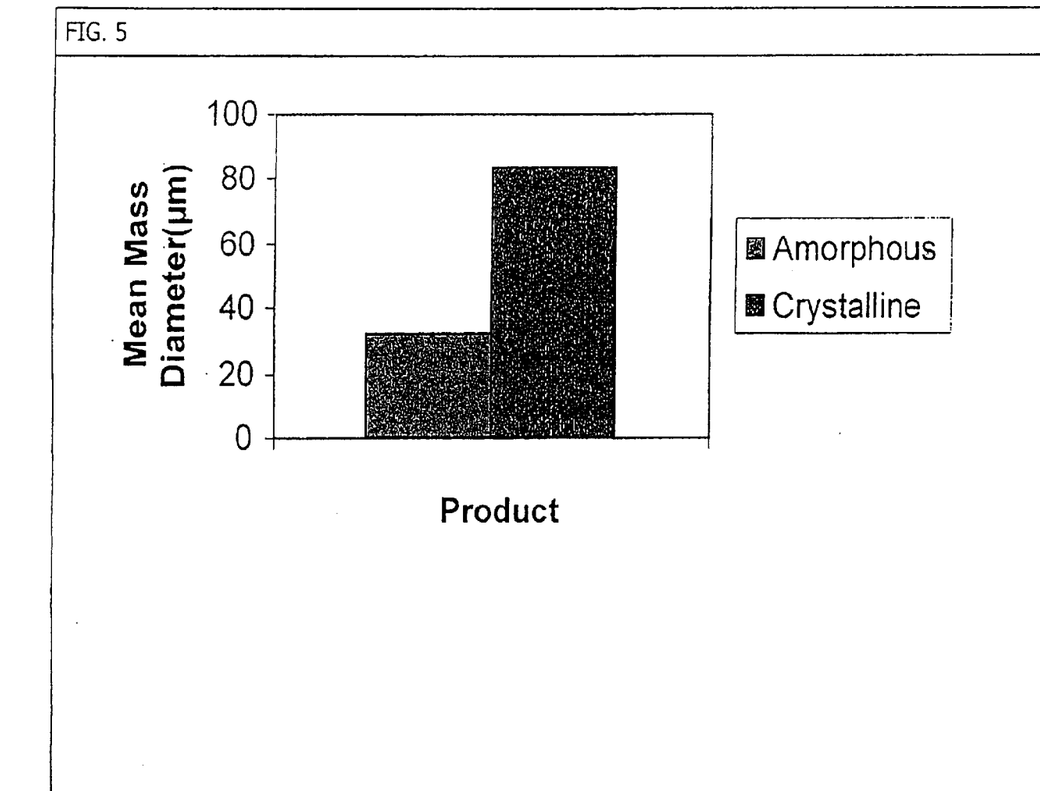
FIG. 5 shows that the particle size measured as mean mass diameter of the substantially crystalline form of S-(−)-9-fluoro-6,7-dihydro-8-(4-hydroxypiperidin-1-yl)-5-methyl-1-oxo-1H,5H-benzo[ij]quinolizine-2-carboxylic acid arginine salt of the invention is ca. 84 μm and the particle size of the substantially amorphous form of S-(−)-9-fluoro-6,7-dihydro-8-(4-hydroxypiperidin-1-yl)-5-methyl-1-oxo-1H, 5H-benzo[i,j]quinolizine-2-carboxylic acid arginine salt of the invention is ca. 32.5 μm.
Figure 6:
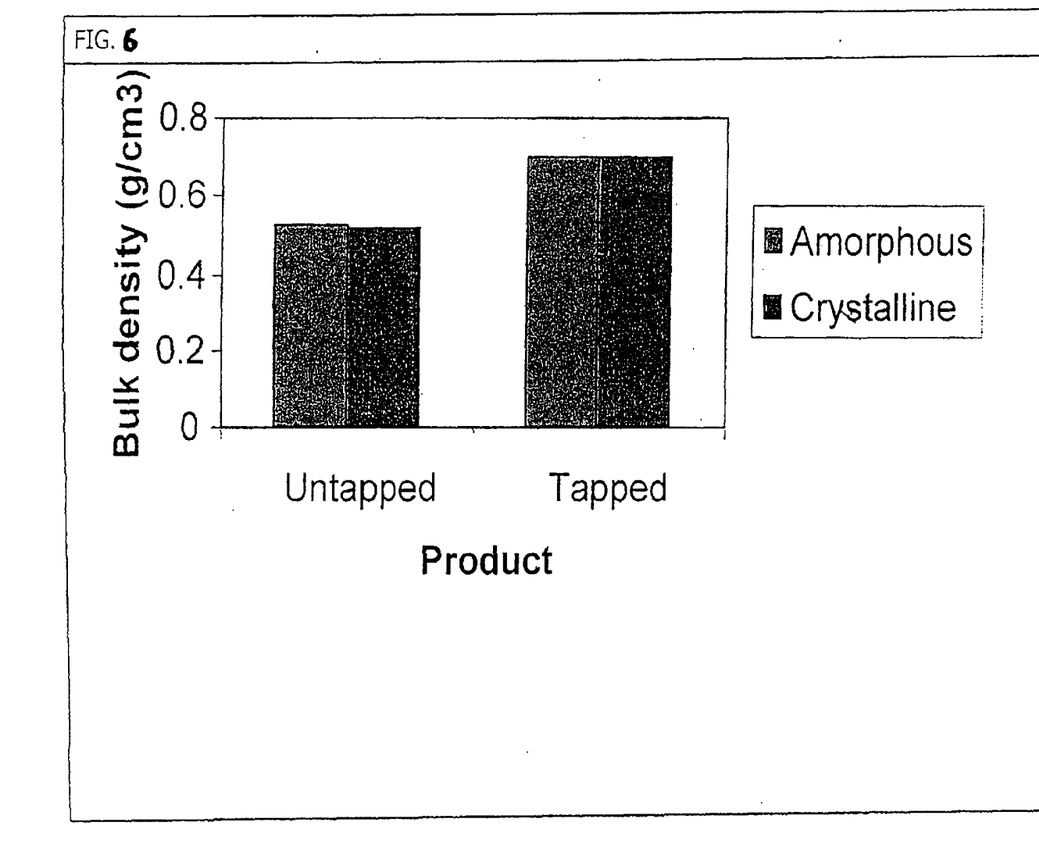
FIG. 6 shows that the density of the substantially crystalline form of the invention is between 0.51 g/cm$^3$ (untapped) and 0.7 g/cm$^3$ (tapped), and the density of the substantially amorphous form of the invention is between 0.52 g/cm$^3$ (untapped) and 0.7 g/cm$^3$ (tapped).

It is desirable that the substantially crystalline form also has the following properties:

(c) Particle size measured as mean mass diameter (MMD) less than 99 µm, preferably less than 85 µm as determined by laser diffraction technique, and as shown in FIG. 5;

(d) Density between 0.51 g/cm³ (untapped) and 0.7 g/cm³ (tapped) As shown in FIG. 6;

(e) Hygroscopicity not exceeding 0.1% increase of weight upon storage for 14 days up to 22% relative atmospheric humidity as determined gravimetrically;

(f) A content of water between 0.1 and 0.2% by weight as determined by titration according to Karl Fischer; and (g) When methyl ethylketone, methylisobutylketone or acetone is used in the preparation of this form, the content of the solvent is less than 0.5%, preferably less than 0.4% by weight as determined by gas chromatography. When acetonitrile is used as solvent, the content of acetonitrile is less than 0.04%, preferably less than 0.03% by weight as determined by gas chromatography.

Figure 2:
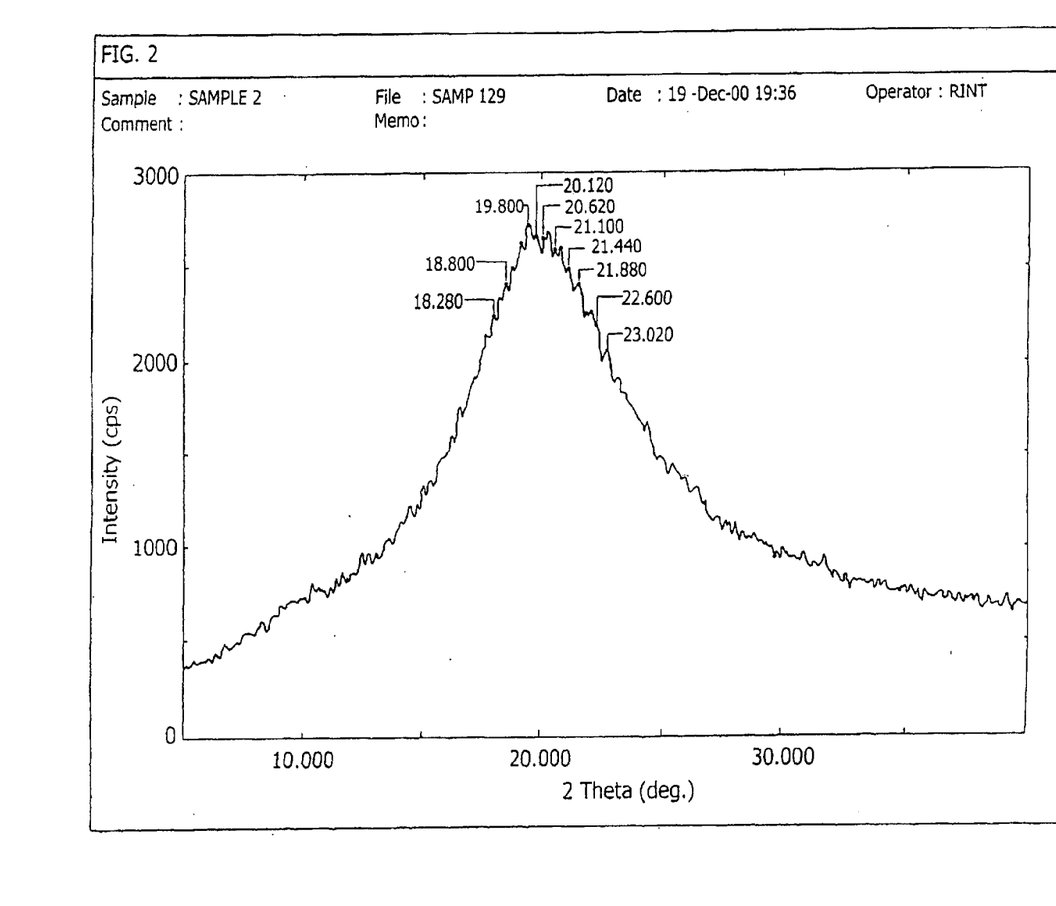
FIG. 2 represents the X-Ray Powder Diffraction (XRPD) spectrum of the substantially amorphous form of S-(−)-9-fluoro-6,7-dihydro-8-(4-hydroxypiperidin-1-yl)-5-methyl-1-oxo-1H,5H-benzo[i,j]quinolizine-2-carboxylic acid arginine salt of the invention.

The substantially amorphous form is described below:

(a) The degree of crystallinity as determined by X-ray powder diffraction is shown in FIG. 2, X-ray powder diffraction (2θ): 18.28, 18.8, 19.8, 20.12, 20.62, 21.10, 21.44, 21.88, 22.6, 23.02.

Figure 4:
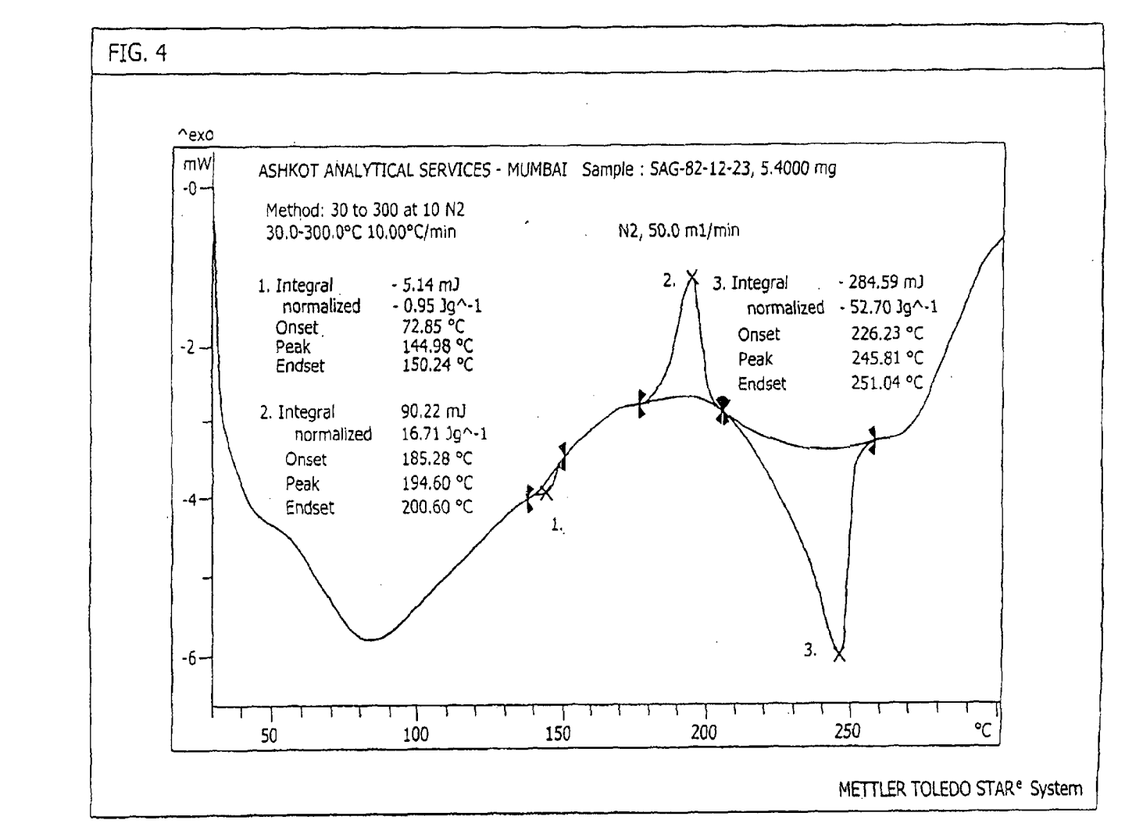
FIG. 4 represents the Differential Scanning Calorimeter (DSC) thermogram of the substantially amorphous form of S-(−)-9-fluoro-6,7-dihydro-8-(4-hydroxypiperidin-1-yl)-5-methyl-1-oxo-1H,5H-benzo[i,j]quinolizine-2-carboxylic acid arginine salt of the invention.

(b) A thermogram as determined by Differential scanning calorimetry is shown in FIG. 4 (DSC endotherm at 194.60° C. (onset at 185.28° C.) and an exotherm at 245.81° C. (onset at 226.23° C.)).

It is desirable that the substantially amorphous form also has the following properties:

(c) Particle size measured as mean mass diameter (MMD) less than 43 µm, preferably less than 34 µm as determined by laser diffraction technique, and as shown in FIG. 5;

(d) Density between 0.52 g/cm³ (untapped) and 0.7 g/cm³ (tapped) as shown in FIG. 6;

(e) Hygroscopicity not exceeding 0.1% increase of weight upon storage for 14 days up to 22% relative atmospheric humidity as determined gravimetrically;

(f) A content of water between 0.4 and 0.7% by weight as determined by titration according to Karl Fischer; and (g) When an alkanol is used as the solvent in the preparation of the substantially amorphous form, the content of solvent is less than 0.3% by weight, preferably less than 0.2% by weight as determined by gas chromatography.

The S-(−)-9-fluoro-6,7-dihydro-8-(4-hydroxypiperidin-1-yl)-5-methyl-1-oxo-1H,5H-benzo [i,j]quinolizine-2-carboxylic acid arginine salt exhibits the same antibacterial activity as the free active ingredient, S-(−)-9-fluoro-6,7-dihydro-8-(4-hydroxypiperidin-1-yl)-5-methyl-1-oxo-1H, 5H-benzo[i,j]quinolizine-2-carboxylic acid.

The substantially crystalline and substantially amorphous forms of S-(−)-9-fluoro-6,7-dihydro-8-(4-hydroxypiperidin-1-yl)-5-methyl-1-oxo-1H,5H-benzo[i,j]-quinolizine-2-carboxylic acid arginine salt anhydrate have antimicrobial activity:

They have potent activity against resistant *Staphylococcus aureus*.

They have ability to resist drug efflux in Gram-positive organisms.

They have the unusual ability to retain potency at an acidic pH of 5.5

They are effective in treating respiratory pathogens.

The are effective in treating resistant mutants.

They have superior cidal action against slow-growing *Staphylococci*.

They score over the standard drugs in terms of eradication efficacy for Staphylococci from vital organs and thigh muscle.

The present invention also relates to a process for preparing the novel polymorphic forms of the arginine salt. A process for the manufacture of the substantially crystalline and substantially amorphous forms of S-(−)-9-fluoro-6,7-dihydro-8-(4-hydroxypiperidin-1-yl)-5-methyl-1-oxo-1H, 5H-benzo[i,j]quinolizine-2-carboxylic acid arginine salt comprises the following consecutive steps:

a) treating S-(−)-9-fluoro-6,7-dihydro-8-(4-hydroxypiperidin-1-yl)-5-methyl-1-oxo-1H,5H-benzo[i,j]quinolizine-2-carboxylic acid with arginine in a solvent mixture composed of water and an organic solvent, to form a solution;

b) concentrating the solution under reduced pressure to provide a residue;

c) treating the residue with an alkane;

d) isolating the substantially crystalline or substantially amorphous form of S-(−)-9-fluoro-6,7-dihydro-8-(4-hydroxypiperidin-1-yl)-5-methyl-1-oxo-1H, 5H-benzo[i,j]quinolizine-2-carboxylic acid arginine salt; and e) purifying and drying the substantially crystalline or substantially amorphous form of S-(−)-9-fluoro-6,7-dihydro-8-(4-hydroxypiperidin-1-yl)-5-methyl-1-oxo-1H, 5H-benzo[i,j]quinolizine-2-carboxylic acid arginine salt using conventional methods.

Preferably the ratio of arginine to S-(−)-9-fluoro-6,7-dihydro-8-(4-hydroxypiperidin-1-yl)-5-methyl-1-oxo-1H, 5H, benzo [i,j] quinolizine-2-carboxylic acid is 1 mole to 1 mole.

Preferably the solvent mixture used in step (a) is composed of water and an organic solvent. When the organic solvent is a ketone or nitrile, the content of water in the solvent mixture is 20%–50%. When the organic solvent is methanol, the content of water in the solvent mixture is 2%–10%; when the organic solvent is ethanol, the water content in the solvent mixture is about 15%; when the organic solvent is isopropanol, the water content in the solvent mixture is about 50%.

Preferably the solution of step (a) is stirred for 30–60 minutes.

Preferably in step (b) the solution is concentrated at 170–180 m bar and then at 40–60 m bar.

In a preferred embodiment, the aqueous solution of arginine is added to a solution of an equimolar amount of S-(−)-9-fluoro-6,7-dihydro-8-(4-hydroxypiperidin-1-yl)-5-methyl-1-oxo-1H,5H-benzo[i,j]quinolizine-2-carboxylic acid in an organic solvent, stirred for 30–60 minutes, and concentrated under reduced pressure, first at 170–180 mbar and then at 40–60 mbar to provide a residue. Organic solvents may be selected from ($C_1$–$C_6$) ketones, ($C_1$–$C_6$) nitrites, or ($C_1$–$C_6$) alkanols and the like. When the organic solvent used is a ketone or nitrile such as methyethylketone, methylisobutylketone, methylbutylketone, acetone or acetonitrile, the residue obtained is substantially crystalline. When the organic solvent used is one such as an alkanol, for example methanol, ethanol or isopropanol, the residue obtained is substantially amorphous. The residue is treated with an alkane such as a ($C_1$–$C_6$) alkane, preferably hexane or pentane. The mixture is stirred for 3–5 hours, and the desired salt isolated by filtration or centrifugation, washed if necessary with additional amounts of alkane, preferably hexane or pentane, and dried preferably under reduced pressure and heating up to 65–70° C.

The process for manufacturing the new forms of S-(−)-9-fluoro-6,7-dihydro-8-(4-hydroxypiperidin-1-yl)-5-methyl-1-oxo-1H, 5H-benzo[i,j]quinolizine-2-carboxylic acid arginine salt differs from the earlier known processes in that it can be controlled to give two different polymorphic forms of the substantially anhydrate salt form through use of the respective solvents that are shown to result in the two forms. This process can be carried out in conventional chemical process equipment and produces a product, which is substantially an anhydrate. It was not possible to obtain these products with known processes.

A comparison between the different samples of the novel forms of the arginine salt prepared by the process of the present invention and those obtained from the experiments disclosed in the prior art shows that the salt of the present invention is substantially an anhydrate, is stable up to 70° C. and at relative humidity up to 22% at 25° C., and has favourable aqueous solubility, all attributes essential to the preparation of pharmaceutical compositions. The novel forms of S-(−)-9-fluoro-6,7-dihydro-8-(4-hydroxypiperidin-1-yl)-5-methyl-1-oxo-1H,5H-benzo[i,j]quinolizine-2-carboxylic acid arginine salt are also stable under typical storage conditions, have good bioavailability in mammals, have lower phlebitis-forming potential on administration to mammals, have low or reduced toxicity, have acceptable disintegration and dissolution rates, and hence are very useful for pharmaceutical manufacturing and for use in medicine. The forms are specially suitable for long-term intravenous therapy in critically ill patients or patients in intensive care units. Injectable preparations of the arginine salt can be readily prepared in view of its availability in a bulk form that remains stable under specified conditions, its favourable aqueous solubility, its ideal suitability in not causing venous inflammation on repeated intravenous administration, and its safety from adverse toxicity.

An S-(−)-9-fluoro-6,7-dihydro-8-(4-hydroxypiperidin-1-yl)-5-methyl-1-oxo-1H,5H-benzo[i,j]quinolizine-2-carboxylic acid arginine salt form of this invention can be present in pharmaceutical formulations as the only active compound or can be combined with other active ingredients such as other antibacterial agents.

The invention therefore also relates to liquid and solid pharmaceutical formulations which comprise the arginine salt of the invention, such as for example, injectable solutions, suspensions, emulsions, tablets, coated tablets, coated tablet cores, capsules, solutions, troches, dispersions, patches, powders, lotions, gels, sprays, pellets, granules, suppositories, hard or soft gelatin capsules, ointments, creams and the like.

The pharmaceutical formulations are prepared in a manner known per se, for example by mixing, stirring, suspending, dispersing, emulsifying, dissolving and the like, the active compounds with or in the pharmaceutical auxiliaries such as a carrier, diluent, solvent or excipient and processing the components to pharmaceutically suitable forms for parenteral, oral, topical, intranasal, buccal or rectal administration and the like.

Pharmaceutical formulations can be formulated together with auxiliaries and additives usually employed in pharmacy, such as tablet binders, fillers, preservatives, tablet disintegrating agents, flow regulating, agents, plasticizers, wetting agents, dispersing agents, emulsifiers, solvents, pH altering additives, flavourings and the like.

The total daily dose range is generally from about 200 mg to about 1500 mg of the arginine salt form. However, the dose may be higher or lower depending on the needs and conditions of the patient.

The following detailed examples serve to more fully illustrate the invention without limiting its scope.

EXAMPLE 1

S-(−)-9-Fluoro-6,7-dihydro-8-(4-hydroxypiperidin-1-yl)-5-methyl-1-oxo-1H,5H-benzo[i,j]quinolizine-2-carboxylic acid arginine salt Synthesis of Substantially Crystalline product A solution of L-(+)-arginine (48.372 g, 0.278 mole) in distilled water (600 ml) was added dropwise over a period of 30 min to the stirred solution/suspension of finely powdered S-(−)-9-fluoro-6,7-dihydro-8-(4-hydroxypiperidin-1-yl)-5-methyl-1-oxo-1H, 5H-benzo[i,j]quinolizine-2-carboxylic acid (100 g, 0.278 mole) in acetone (1250 ml). The obtained clear solution was stirred for 30 min and concentrated on a water bath in vacuum (175 mbar) at 80° C. When product started solidifying, the concentration was carried out in vacuum (50 mbar) at 80° C. up to dryness. Hexane (1 liter) was added, the reaction mixture was stirred for 4 hr, the solid thus separated was filtered and dried in vacuum (0.7 mbar) for 12 hrs at 70° C. Yield 145 g (96.9%), m.p. 238–242° C., and solubility 6 mg/ml (pH 9.5 buffer solution).

The substantially crystalline S-(−)-9-fluoro-6,7-dihydro-8-(4-hydroxypiperidin-1-yl)-5-methyl-1-oxo-1H,5H-benzo[i,j]quinolizine-2-carboxylic acid arginine salt prepared according to Example 1 possesses the following properties:

a) Crystalline form, with a degree of crystallinity as determined by X-ray powder diffraction and as shown in FIG. 1.

b) A thermogram as determined by Differential scanning calorimetry and as shown in FIG. 3.

c) Particle size measured as mean mass diameter (MMD) of 83.92 μm, as determined by laser diffraction technique.

d) Density of 0.51 g/cm$^3$ (untapped) and 0.7 g/cm$^3$ (tapped).

e) Hygroscopicity of 0% increase of weight upon storage for 14 days up to 22% relative atmospheric humidity as determined gravimetrically.

f) A content of moisture water of 0.1% by weight as determined by titration according to Karl Fischer.

g) A content of acetone of 0.014% by weight as determined by gas chromatography.

EXAMPLE 2

Similarly, when acetonitrile was used in place of acetone in the process described in Example 1, and the amount of water in the resulting acetonitrile-water solution was about 40%, a substantially crystalline product was obtained. Yield 87%.

EXAMPLE 3

Synthesis of Substantially Amorphous Product

When methanol was used in place of acetone in the process described in Example 1, and the amount of water in the resulting methanol-water solution was between 2% to 10%, a substantially amorphous product was obtained. Yield 97.3%, m.p. 238–244° C., $[\alpha]_D^{25}$ −166.2° (c=1, methanol), and solubility 40 mg/ml in pH 9.5 buffer solution.

The novel form of the substantially amorphous S-(−)-9-fluoro-6,7-dihydro-8-(4-hydroxypiperidin-1-yl)-5-methyl-1-oxo-1H,5H-benzo[i,j]quinolizine-2-carboxylic acid arginine salt according to Example 3 possesses the following properties:

a) Amorphous form, with a degree of crystallinity as determined by X-ray powder diffraction and as shown in FIG. 2.

b) A thermogram as determined by Differential scanning calorimetry and shown in FIG. 4.

c) Particle size measured as mean mass diameter (MMD) of 32.44 μm, as determined by laser diffraction technique.

d) Density of 0.52 g/cm$^3$ (untapped) and 0.7 g/cm$^3$ (tapped).

e) Hygroscopicity of 0% increase of weight upon storage for 14 days up to 22% relative atmospheric humidity as determined gravimetrically.

f) A content of moisture water of 0.41% by weight as determined by titration according to Karl Fischer.

h) A content of methanol of 0.16% by weight as determined by gas chromatography.

EXAMPLE 4

Substantially amorphous product was also obtained, when ethanol was used in place of acetone in the process described in Example 1 and the amount of water in the resulting ethanol-water solution was 13–15%. Yield 97.44%.

EXAMPLE 5

Similarly, when isopropanol was used in place of acetone as described in the process of Example 1, and the amount of water in the resulting isopropanol-water solution was about 50%, a substantially amorphous product was obtained. Yield 80%.

EXAMPLE 6

Test Example

X-ray Diffraction Analysis 300 mg each of S-(−)-9-fluoro-6,7-dihydro-8-(4-hydroxypiperidin-1-yl)-5-methyl-1-oxo-1H,5H-benzo [I,j] quinolizine-2-carboxylic acid L-(+)arginine salt prepared as in Examples 1 and 5 were thinly spread on a sample holder. X-ray diffraction analyses (40 kv×40 mA Rigaku D/max 2200) were performed under the conditions listed below:

Scan speed 5°/min

Sampling time 7 min

Scan mode: continuous

2θ/θreflection

Cu target (Ni filter)

Results of the X-ray diffraction analysis on the substantially crystalline and substantially amorphous forms are depicted in FIG. 1 and FIG. 2 respectively. From these spectra it can be verified that their crystal forms differ from each other.

EXAMPLE 7

Test Example

Thermal Analysis of the S-(−)-9-fluoro-6,7-dihydro-8-(4-hydroxypiperidin-1-yl)-5-methyl-1-oxo-1H,5H-benzo [I,j] quinolizine-2-carboxylic acid L-(+)-arginine salts prepared as in Examples 1 and 5.

For the Differential Scanning Calorimetry, METTLER TOLEDO STAR system was used. 5.4 mg of the sample was weighed into the aluminum pan, which was then press sealed with an aluminium lid. After three tiny needle holes were made on the lid the sample was tested by heating from (30° C.) to (300° C.) at a rate of 10° C./min. As can be seen from FIG. 4 (amorphous form) there is an endothermic peak which begins at around 185° C. to 200° C. and an exothermic peak due to thermal decomposition at around 226° C. to 251° C. In contrast the substantially crystalline form (FIG. 3) shows only an exothermic peak at around 208° C. to 256° C. without any endothermic peak.

EXAMPLE 8

Test Example

Bulk Density Determination

For untapped and tapped density determination Bulk Density Apparatus (R.V. Electronics, Mumbai) was used. 25 g of the sample was slowly poured into a dry clean stoppered measuring cylinder and filled volume was measured to obtain untapped density.

Untapped density=25 g/untapped volume.

Then the measuring cylinder was fixed to Bulk Density Apparatus and sample was tapped (150 times) and volume was measured to furnish the tapped volume.

Tapped density=25 g/Tapped volume.

EXAMPLE 9

Test Example

Mean Mass Determination

For mean mass diameter Master Sizer of Malvern Instrument LTD U.K. was used under the conditions listed below:

Lens/Focus: 300 mm

Solvent: Hexane

Analysis model: Polydisperse

Obstruction value: 20–23%

Results are depicted in FIG. 5.

What is claimed is:

1. A solid composition comprising S-(1)-9-fluoro-6,7-dihydro-8-(4-hydroxypiperidin-1-yl)-5-methyl-1-oxo-1H,5H-benzo[i,j]quinolizine-2-carboxylic acid arginine salt having the following X-ray diffraction data: (2θ): 10.16, 11.78, 12.52, 16.00, 18.94, 19.66, 20.36, 21.28, 21.92, 22.52, 24.74, 25.28, 30.74 and a solid carrier, diluent, or excipient.

2. A solid composition comprising S-(−)-9-fluoro-6,7-dihydro-8-(4-hydroxypiperidin-1-yl)-5-methyl-1-oxo-1H,5H-benzo[i,j]quinolizine-2-carboxylic acid arginine salt having the following X-ray diffraction data (2θ): 18.28, 18.8, 19.8, 20.12, 20.62, 21.10, 21.44, 21.88, 22.6, 23.02 and a solid carrier, diluent, or excipient.

3. A method for treating a disease caused by a microbial infection in a mammal comprising administering an effective amount of a composition according to claim 1 to a mammal in need thereof.

4. A method for treating a disease caused by a microbial infection in a mammal comprising administering an effective amount of a composition according to claim 2 to a mammal in need thereof.

* * * * *

Disclaimer

6,753,333 — Noel J. De Souza; Shivkumar Agarwal; Mahesh V. Patel; Satish B. Bhawsar; Rupinder K. Beri; Ravindra D. Yeole; Nitin Shetty; all of Chikaltana (IN). CHIRAL FLUOROQUINOLONE ARGININE SALT FORMS. Patent dated June 22, 2004. Disclaimer filed August 24, 2004, by the assignee, Wockhardt Limited.

The term of this patent, subsequent to the term of patent number, 6,514,986 has been disclaimed.

*(Official Gazette, November 2, 2004)*